United States Patent
Craven et al.

(10) Patent No.: US 6,469,187 B1
(45) Date of Patent: Oct. 22, 2002

(54) CONTAMINANT REDUCED MARINE OIL

(75) Inventors: Charles W. Craven, Hull (GB); Tommy Morrison, Cottingham (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/701,841

(22) PCT Filed: May 27, 1999

(86) PCT No.: PCT/EP99/03657

§ 371 (c)(1),
(2), (4) Date: Dec. 5, 2000

(87) PCT Pub. No.: WO99/64547

PCT Pub. Date: Dec. 16, 1999

(30) Foreign Application Priority Data

Jun. 5, 1998 (EP) ............................................. 98110244

(51) Int. Cl.$^7$ .................................................. C11B 3/00
(52) U.S. Cl. ........................................................ 554/195
(58) Field of Search ........................................ 554/195

(56) References Cited

FOREIGN PATENT DOCUMENTS

| EP | 196402 | | 10/1986 |
|----|--------|---|---------|
| EP | 340635 | * | 11/1989 |
| JP | 1099518 | | 4/1989 |

OTHER PUBLICATIONS

Krukonis et al., JAOCS, vol. 66, No. 6, pp. 818–821, 1989.*
Brevik et al., Organohalogen Compounds, No. 1, pp. 467–470, 1990.*
Addison et al., JAOCS, vol. 51, No. 5, pp. 192–194, 1974.*
Hilbert et al., Chemosphere, nol. 37, No. 7, pp., 1241–1252, 1998.*
FSTA abstr. of JOJOC, vol. 25, No. 1, pp., 38–41, 1976.*
Swern D.: "Bailey's industrial oil and fat products", John Wiley & Sons, New York XP002085012 p. 254–255 p. 288–289 p. 294–295.
Miller J et al: "ISF/AOCS World congress." Journal of the American Oil Chemists' Society, vol. 57, No. 2, 1980, pp. 79A–191A, XP002085008.
Brevik E.M., Biseth A., Oehme M.: "Levels of polychlorinated dibenzofurans and dibenzo–p–dioxins in crude and processed fish oils in relation to origin and cleaning method" Organohalogen compounds, No. 1, 1990, p. 467–470 XP002086193 cited in the application.
Krukonis V J ISBN 0–913250–73–2: "Supercritical fluid processing of fish oils: extraction of polychlorinated biphenyls." Journal of the American Oil Chemists' Society, vol. 66, No. 6, 1989, pp. 818–821, XP002085009 Phasex Corp., 360 Merrimack Street, Lawrence, MA 01843, USA cited in the application.
Addison R F et al: "Removal of organochlorine pesticides and polychlorinated biphenyls from marine oils during refining and hydrogenation for edible use." Journal of the American Oil Chemists' Society, vol. 51, No. 5, 1974, pp. 192–194, XP002085010 Fisheries Res. Board of Canada, Marine Ecology Lab., Bedford Inst. of Oceanography, Dartmouth, Nova Scotia B2Y 4A2 cited in the application.
Hilbert G., Lillemark L., Balchen S., Schriver Hojskov C.; "Reduction of organochlorine contaminants from fish oil during refining" Chemosphere, vol. 37, No. 7, 1998, pp. 1241–1252 XP002085011.
Database FSTA [Online] International Food Informations Service (IFIS), Franfurt/Main, DE "Dioxins and Polychlorinated Biphenyls in Fish Oil Dietary Supplements and Licensed Medicines." XP002085014 & Food Surveillance Information Sheet, Ministry of Agriculture, Fisheries and Food, 1997, MAFF, 17 Smith Square, London SWIP 3J.
Database FSTA [Online] International Food Informations Service (IFIS), Franfurt/Main, DE Kanematsu H et al: "Behaviour of Trace Components in Oils and Fats During Processing for Edible Use. I. Removal of Organochlorine Pesticides and Polychlorinated Biphenyls (PCB) from Oils and Fats." XP002085013 & Journal of Japan Oil Chemists' Society ((Yukagaku)), vol. 25, No. 1, 1976, pp. 38–41, Japan Inst. of Oils & Fats, 27–8, 3–Chome, Nihonbashi–Hamacho, Chuo–Ku, Tokyo, Japan.
Database WPI Section Ch, Week 8921 Derwent Publications Ltd., London, GB; Class D13, AN 89–156508 XP002085015 & JP 01 099518 A (Nippon Light Metal Co), Apr. 18, 1989.

* cited by examiner

Primary Examiner—Deborah D. Carr
(74) Attorney, Agent, or Firm—Millen, White, Zelano & Branigan, P.C.

(57) ABSTRACT

Process for the preparation of oil of marine origin with reduced content of polychlorinated dioxins, furans, biphenyls and polycyclic aromatic hydrocarbons.

The oil obtainable by the process has combined concentrations of polychlorinated dioxins, furans and biphenyls in a range from 0.05–6 (ng TEQ/kg oil) and is used in foodstuffs or pharmaceutical formulations.

27 Claims, No Drawings

CONTAMINANT REDUCED MARINE OIL

This application is a 511 of PCT/EPAa/03657 filed May 27, 1999.

The present invention relates to a process for the preparation of oil of marine origin with reduced content of polychlorinated dioxins, furans, biphenyls, and polycyclic aromatic hydrocarbons. This invention also relates to a composition of matter obtained by the process and the use thereof.

A method for reducing the content of PCBs in fish oil by means of silica gel or silicic acid is known from EP 0 340 635. R. F. Addison et al. describes the removal of Organochlorine Pesticides and Polychlorinated Biphenyls from Marine Oils by means of clay in J. Amer. Oil Chem. Soc. 51, 192–194 (1974). Product shown 0.5 ppm polychlorinated biphenyls as a result of such processing. V. J. Krukonis describes the extraction of polychlorinated biphenyls by means of supercritical fluid processing of fish oils in J. Amer. Oil Chem. Soc. 66, 818–821 (1989). Obtained products have PCB concentrations of about 10 ppm. Levels of polychlorinated dibenzofurans (PCDF) and dibenzo-p-dioxins (PCDD) in crude and processed fish oils are described by E. M. Brevik et al., Organohalogen Compounds (1990), 1, 467–70. It is pointed out that neither deodorisation by steam stripping nor filtration through adsorbents is able to reduce the levels of any of the PCDD/PCDF isomers. The paper by Els G. van der Veide et al. relates to methodology for the analysis of PCBs in oils and describes supercritical fluid extraction as clean-up technique of PCBs in fatty samples in Organohalogen Compounds (1996), 27, 247–52. The process uses up to 2 g of fish oil and not the processing of bulk oils for the removal of these compounds.

Combined concentrations of dioxins and PCBs in cod liver oil were published in Food Surveillance Information Sheet, Vol. 106, June 1997, MAFF, London.

Where full data were obtained, the combined concentrations of dioxins and PCBs in cod liver ranged from 18–41 (ng TEQ/kg oil) in 1996.

Due to a change in the traditional approach to the assessment of toxicity of a specific group of organochlorine environmental contaminants by the WHO, it has proved necessary to develop a method of eliminating these contaminants from marine oil products.

The invention was based on the object of finding contaminant reduced marine oils having useful properties, in particular those which can be used in foodstuffs or pharmaceutical formulations.

It has been found that the fish body oils, obtainable by the inventive process, have very useful properties, in particular, they exhibit extremely reduced contents of polychlorinated contaminants.

"Dioxins" is the generic term given to polychlorinated dibenzo-p-dioxins and dibenzofurans. Dioxins are unwanted by-products in the manufacture of certain chemicals. Small amounts are also produced during most combustion and incineration processes. PCBs (polychlorinated biphenyls) are a group of 209 related compounds known as congeners. Advances in analytical methodology have allowed to separate and to quantify individual congeners. Appropriate methods now exist to quantify the separation of said contaminants. However, such analysis would be prohibitively costly and therefore specific congeners are usually selected for analysis.

Polychlorinated dioxins and polychlorinated furans means polychlorinated dibenzo-p-dioxins and polychlorinated dibenzofurans.

Dioxins and furans have for some time been calculated in terms of a toxic equivalency (TEQ) related to the reportedly most toxic congener (2,3,7,8-TCDD). The change referred to above is the range of PCB congeners have now also been assigned toxic equivalency factors. The results for all three classes of compounds are now converted to TEQs and are added together to give a total TEQ. The addition of the PCBs to the calculation has significantly raised the TEQ values found in marine oils and in particular cod liver oil, whilst the tolerable daily intake for these compounds, also set by the WHO, has not been altered.

Surprisingly, the process reduces the total TEQ in the product by 90% in comparison to the natural fish oil.

The present invention relates to a process for the preparation of oil of marine origin with reduced content polychlorinated dioxins, furans, biphenyls, and polycyclic aromatic hydrocarbons, characterized in that the marine oil a) is refined with acid and/or alkali, b) is cold cleared, c) is stirred under reduced pressure in the temperature range of 40 to 100° C. with activated carbon, d) is cooled to 20 to 40° C., e) is separated off the activated carbon, f) is deodorised with hot steam under reduced pressure for a period of 0.5 hour to 20 hours, g) and is cooled to 20 to 70° C.

The present invention preferably relates to a process for the preparation of fish body oil and most preferably of cod liver oil with reduced content of polychlorinated dioxins, furans and biphenyls.

Furthermore, the invention relates to the oils obtainable by the inventive processes which exhibit combined concentrations of polychlorinated dioxins, furans and biphenyls in the range of 0.05–6 (ng TEQ/kg oil), preferably in the range of 0.5–5 (ng TEQ/kg oil), most preferably in the range 1–4 (ng TEQ/kg oil).

Moreover, the present invention relates to the oil of marine origin obtainable by the inventive process, with a concentration of polychlorinated dioxins in the range 0.01–0.3 (ng TEQ/kg oil), preferably in the range 0.03–0.22 (ng TEQ/kg oil), to an oil with a concentration of polychlorinated furans in the range 0.01–0.1 (ng TEQ/kg oil), preferably in the range 0.03–0.08 (ng TEQ/kg oil), to an oil with a concentration of polychlorinated biphenyls in the range 0.01–5 (ng TEQ/kg oil), preferably in the range 0.1–4 (ng TEQ/kg oil), and to an oil with a concentration of polycyclic aromatic hydrocarbons (PAH) in the range 0.005–0.4 (BAP-equivalents [$\mu$g/kg]), preferably in the range 0.01–0.35 (BAP-equivalents [$\mu$g/kg]). The present invention is not related to the analytical limits of determination, but relates to specific dioxin, furan and PCB congeners (those assigned a toxic equivalency factor) and their removal from and the residual levels in commercial quantities of marine oils.

Table 1 lists the chlorine-containing contaminants names.

TABLE 1

| Contaminant |
| --- |
| Polychlorinated dibenzo-p-dioxins |
| 2,3,7,8-tetrachlorodibenzo-p-dioxin (-TCDD) |
| 1,2,3,7,8-pentachlorodibenzo-p-dioxin (-PeCDD) |
| 1,2,3,4,7,8-hexachlorodibenzo-p-dioxin (-HxCDD) |
| 1,2,3,6,7,8-hexachlorodibenzo-p-dioxin (-HxCDD) |
| 1,2,3,7,8,9-hexachlorodibenzo-p-dioxin (-HxCDD) |
| 1,2,3,4,6,7,8-heptachlorodibenzo-p-dioxin (-HpCDD) |
| Octachlorodibenzo-p-dioxin |

TABLE 1-continued

Contaminant

Polychlorinated dibenzofurans 2,3,7,8-tetrachlorodibenzofuran (-TCDF)
1,2,3,7,8-pentachlorodibenzofuran (-PeCDF)
2,3,4,7,8-pentachlorodibenzofuran (-PeCDF)
1,2,3,4,7,8-hexachlorodibenzofuran (-HxCDF)
1,2,3,6,7,8-hexachlorodibenzofuran (-HxCDF)
1,2,3,7,8,9-hexachlorodibenzofuran (-HxCDF)
2,3,4,6,7,8-hexachlorodibenzofuran (-HxCDF)
1,2,3,4,6,7,8-heptachlorodibenzofuran (-HpCDF)
1,2,3,4,7,8,9-heptachlorodibenzofuran (-HpCDF)
Octachlorodibenzofuran (OCDF)

Polychlorinated biphenyls 3,3',4,4'-tetrachlorobiphenyl (PCB 77)
3,3',4,4',5-pentachlorobiphenyl (PCB 126)
3,3',4,4',5,5'-hexachlorobiphenyl (PCB 169)
2,3,3',4,4'-pentachlorobiphenyl (PCB 105)
2,3,4,4',5-pentachlorobiphenyl (PCB 114)
3,3',4,4',5-pentachlorobiphenyl (PCB 118)
2',3,4,4',5-pentachlorobiphenyl (PCB 123)
2,3,3',4,4',5-hexachlorobiphenyl (PCB 156)
2,3,3',4,4',5'-hexachlorobiphenyl (PCB 157)
2,3',4,4',5,5'-hexachlorobiphenyl (PCB 167)
2,3,3',4,4',5,5'-heptachlorobiphenyl (PCB 189)
2,2',3,4,4',5,5'-heptachlorobiphenyl (PCB 180)

The fish oil with reduced content of contaminants can be obtained preferably by the following process:

a) The fish oil is first refined. Oil is heated via a heat exchanger and phosphoric acid is added followed by sodium hydroxide in a short mix refining plant. The oil is then water washed twice and vacuum tried.

b) The oil is then "cold cleared". Refined oil is cooled in a stirred vessel until it deposits a solid fraction referred to in the industry as stearin. The oil slurry is then filtered through a filter press in a cold environment in order to remove the stearin. The liquid filtrate in known as olein and is the "cold cleared" oil.

c) The oil is charged into a batch vessel fitted with steam heating coils, cooling coils, steam ejector vacuum equipment and a vacuum sealed mechanical stirrer. A vacuum of 0.5 to 60 mbar, preferably 2 to 30 mbar, most preferably 5 to 20 mbar, is raised on the vessel and 0.1 to 5.0% (w/w), preferably 0.2 to 4.0% (w/w), most preferably 0.5 to 2.5% (w/w) powdered activated carbon (of a commercially available grade, e.g. Pulsorb RB ex. Chemviron Carbon Ltd) is added and stirred into the oil. The temperature is then raised to 40 to 100° C., preferably 50 to 80° C. The oil and the carbon are stirred and held at this temperature for 5 to 240 minutes, preferably for 10 to 100 minutes, most preferably for 20 to 50 minutes.

d) The oil is then cooled to 20 to 40° C. The vacuum is released and the mixture is discharged from the vessel.

e) 0.5 to 2.5% (w/w) of filter aid (of a commercially available grade) is then added and the mixture is stirred. The mixture is then filtered through a filter, e.g. a vertical leaf "Niagara" type, to remove the carbon and filter aid.

f) The product is then deodorised. The oil is charged into a deodorisation vessel equipment with heating and cooling coils, steam spray coils and a steam ejection vacuum system. A vacuum of 0.5 to 60 mbar, preferably 1 to 20 mbar, most preferably 2 to 5 mbar, is then pulled over the oil and the oil is heated to 100 to 250° C., preferably 140 to 230° C., most preferably 170 to 220° C. Steam is then purged through the oil using the steam spray coils and these conditions are maintained for 0.5 to 20 hours, preferably 1 to 10 hours, most preferably 2 to 6 hours.

g) Steam purging then ceases and the oil is cooled to 40–60° C. at which time any vitamin or other additions are made. Vacuum is then broken and the oil is discharged to the finished product storage tanks.

EXAMPLE

The following example demonstrates the reduction in organochlorine contaminants and polycyclic aromatic hydrocarbons achievable using the process as outlined above. Analyses were performed analogous to Food Surveillance Information Sheet, Vol. 106, June 1997, MAFF, London and the references cited therein.

TABLE 2

| Contaminant | Level in Refined, Cold Cleared Oil | Level in Fully Processed Oil |
|---|---|---|
| Dioxins (content of individual congeners in ng/kg) | | |
| 2,3,7,8-TCDD | 1.72 | 0.06 |
| 1,2,3,7,8-PeCDD | 1.09 | <0.05 |
| 1,2,3,4,7,8-HxCDD | <0.23 | <0.07 |
| 1,2,3,6,7,8-HxCDD | 3.24 | <0.07 |
| 1,2,3,7,8,9-HxCDD | 0.70 | <0.08 |
| 1,2,3,4,6,7,8-HpCDD | 2.06 | <0.14 |
| OCDD | 4.26 | 1.34 |
| TEQ for Dioxins [ng/kg] | 2.71 | 0.11 |
| Furans (content of individual congeners in ng/kg) | | |
| 2,3,7,8-TCDF | 21.53 | 0.03 |
| 1,2,3,7,8-PeCDF | 6.24 | <0.03 |
| 2,3,4,7,8-PeCDF | 5.04 | <0.04 |
| 1,2,3,4,7,8-HxCDF | 1.85 | <0.05 |
| 1,2,3,6,7,8-HxCDF | 20.90 | <0.05 |
| 1,2,3,7,8,9-HxCDF | <0.23 | <0.07 |
| 2,3,4,6,7,8-HxCDF | 2.99 | <0.06 |
| 1,2,3,4,6,7,8-HpCDF | 1.29 | <0.10 |
| 1,2,3,4,7,8,9-HpCDF | 0.24 | <0.17 |
| OCDF | 1.01 | <0.67 |
| TEQ for Furans [ng/kg] | 7.60 | 0.05 |
| PCBs (content of individual congeners in µg/kg) | | |
| PCB 77 | 0.433 | 0.0057 |
| PCB 126 | 0.392 | 0.0045 |
| PCB 169 | 0.108 | 0.0022 |
| PCB 105 | 14.780 | 1.460 |
| PCB 114 | 0.910 | 0.100 |
| PCB 118 | 44.970 | 3.390 |
| PCB 123 | 1.370 | 0.130 |
| PCB 156 | 4.640 | 1.150 |
| PCB 157 | 1.340 | 0.340 |
| PCB 167 | 2.380 | 0.510 |
| PCB 189 | <0.10 | <0.10 |
| PCB 180 | 22.580 | 11.280 |
| TEQ for PCBs [ng/kg] | 50.33 | 1.90 |
| Total TEQ [ng/kg] | 60.64 | 2.06 |

The concentrations of PAHs are determined by capillary gas chromatography-mass spectrometry and quantified by reference to $^{13}C$ internal standards. Results are given in µg/kg (Table 3) for individual compounds and also as benzo-(a)-pyrene (BAP) equivalents (Table 4).

TABLE 3

Analytical Results [µg/kg]

| Compounds | Sample* 1 | 2 | 3 | 4 |
|---|---|---|---|---|
| acenaphthalene | 0.26 | 0.11 | 0.10 | 0.10 |
| acenaphthene | 5.97 | 0.66 | 0.54 | 0.66 |
| fluorene | 7.78 | 0.56 | 0.51 | 0.55 |
| anthracene | 18.22 | 1.17 | 1.35 | 1.31 |
| phenanthrene | <0.03 | <0.03 | 0.08 | <0.03 |
| fluoranthene | 2.86 | 0.29 | 0.45 | 0.30 |
| pyrene | 3.15 | 0.32 | 0.71 | 0.34 |
| benz-(a)-anthracene | 0.55 | 0.09 | 0.07 | 0.09 |
| chrysene | 2.44 | 0.15 | 0.15 | 0.17 |
| benzo-(b)-fluoranthene | 0.24 | 0.04 | <0.02 | <0.02 |
| benzo-(k)-fluoranthene | 0.18 | <0.02 | <0.02 | <0.02 |
| benzo-(a)-pyrene | 0.18 | <0.01 | <0.01 | <0.01 |
| indeno-(1,2,3-cd)-pyrene | <0.01 | <0.01 | <0.01 | <0.01 |
| dibenz-(ah)-anthracene | <0.001 | <0.001 | <0.001 | <0.001 |
| benzo-(g,h,i)-perylene | <0.02 | <0.02 | <0.02 | <0.02 |

*1 = feedstock
2, 3, 4 = level in fully processed oil

TABLE 4

Benzo-(a)-pyrene equivalents [µg/kg]*

| Compounds | Sample** 1 | 2 | 3 | 4 |
|---|---|---|---|---|
| acenaphthalene | 0.000 | 0.000 | 0.000 | 0.000 |
| acenaphthene | 0.006 | 0.001 | 0.001 | 0.001 |
| fluorene | 0.008 | 0.001 | 0.001 | 0.001 |
| anthracene | 0.182 | 0.012 | 0.013 | 0.013 |
| phenanthrene | 0.000 | 0.000 | 0.000 | 0.000 |
| fluoranthene | 0.003 | 0.000 | 0.000 | 0.000 |
| pyrene | 0.003 | 0.000 | 0.001 | 0.000 |
| benz-(a)-anthracene | 0.055 | 0.009 | 0.007 | 0.009 |
| chrysene | 0.024 | 0.001 | 0.001 | 0.002 |
| benzo-(b)-fluoranthene | 0.024 | 0.004 | 0.000 | 0.000 |
| benzo-(k)-fluoranthene | 0.018 | 0.000 | 0.000 | 0.000 |
| benzo-(a)-pyrene | 0.176 | 0.000 | 0.000 | 0.000 |
| indeno-(1,2,3-cd)-pyrene | 0.000 | 0.000 | 0.000 | 0.000 |
| dibenz-(ah)-anthracene | 0.000 | 0.000 | 0.000 | 0.000 |
| benzo-(g,h,i)-perylene | 0.000 | 0.000 | 0.000 | 0.000 |
| Total BAP equivalent | 0.499 | 0.028 | 0.025 | 0.026 |

*calculated with reference to I.C.T. Nisbet et al. (1992) Toxic Equivalency Factors (TEFs) for Polycyclic Aromatic Hydrocarbons (PAHs). Regulatory Toxicology and Pharmacology 16, 290–300
**1 = feedstock
2, 3, 4 = level in fully processed oil

What is claimed is:

1. A process for the preparation of oil of marine origin with reduced content of polychlorinated dioxins, furans, biphenyls, and polycyclic aromatic hydrocarbons, comprising:

a) refining marine oil with acid and/or alkali, b) cold clearing the marine oil, c) stirring the marine oil under reduced pressure at a temperature of 40 to 100° C. with activated carbon, d) cooling the marine oil to 20 to 40° C., e) separating the activated carbon from the marine oil, f) deodorizing the marine oil with hot steam under reduced pressure for a period of 0.5 hour to 20 hours, and g) cooling the marine oil to 20 to 70° C.

2. A process according to claim 1, wherein said marine oil is fish body oil.

3. A process according to claim 2, wherein said marine oil is cod liver oil.

4. A process according to claim 1, wherein the level of activated carbon added to the marine oil is 0.1 to 5.0% (w/w).

5. A process according to claim 1, wherein c) is carried out at a pressure of 0.5 to 60 mbar for 5 to 240 minutes.

6. A process according to claim 1, wherein the oil is deodorized at a temperature of 100 to 250° C. and under a pressure of 0.5 to 60 mbar.

7. An oil of marine origin with reduced content of polychlorinated dioxins, furans and biphenyls, and polycyclic aromatic hydrocarbons obtainable by the process of claim 1.

8. Oil of marine origin according to claim 7 wherein the oil is cod liver oil.

9. Oil of marine origin according to claim 7 with a concentration of polychlorinated dioxins in the range 0.01–0.3 (ng TEQ/kg oil).

10. Oil of marine origin according to claim 7 with a concentration of polychlorinated furans in the range 0.01–0.1 (ng TEQ/kg oil).

11. Oil of marine origin according to claim 7 with a concentration of polychlorinated biphenyls in the range 0.01–5 (ng TEQ/kg oil).

12. Oil of marine origin according to claim 7 with combined concentrations of polychlorinated dioxins, furans and biphenyls in the range (0.05–6 (ng TEQ/kg oil).

13. Oil of marine origin according to claim 7 with a concentration of polycyclic aromatic hydrocarbons in the range 0.005–0.4 (BAP-equivalents [µg/kg]).

14. In a foodstuff containing an oil of marine origin, the improvement wherein said is an oil according to claim 1.

15. A process according to claim 1, wherein said activated carbon is powdered.

16. A process according to claim 4, wherein said activated carbon is powdered.

17. In a pharmaceutical formulation containing an oil of marine origin, the improvement wherein said oil is an oil according to claim 1.

18. A process according to claim 1, wherein the resultant marine oil exhibits a combined concentration of polychlorinated dioxins, furans, and biphenyls of 0.05–6 ng TEQ/kg oil.

19. A process according to claim 1, wherein the resultant marine oil exhibits a combined concentration of polychlorinated dioxins, furans, and biphenyls of 0.5–5 ng TEQ/kg oil.

20. A process according to claim 1, wherein the resultant marine oil exhibits a combined concentration of polychlorinated dioxins, furans, and biphenyls of 1–4 ng TEQ/kg oil.

21. A process according to claim 1, wherein the resultant marine oil exhibits a concentration of polychlorinated dioxins of 0.01–0.3 ng TEQ/kg oil, a concentration of polychlorinated furans of 0.01–0.1 ng TEQ/kg oil, a concentration of polychlorinated biphenyls of 0.01–5 ng TEQ/kg oil, and a concentration of polycyclic aromatic hydrocarbons of 0.005–0.4 µg/kg in terms of BAP-equivalents.

22. A process according to claim 1, wherein the resultant marine oil exhibits a concentration of polychlorinated dioxins of 0.03–0.22 ng TEQ/kg oil, a concentration of polychlorinated furans of 0.03–0.08 ng TEQ/kg oil, a concentration of polychlorinated biphenyls of 0.1–4 TEQ/kg oil, and a concentration of polycyclic aromatic hydrocarbons of 0.01–0.35 µg/kg in terms of BAP-equivalents.

23. An oil of marine origin according to claim 7, wherein said marine oil exhibits a concentration of polychlorinated dioxins of 0.01–0.3 ng TEQ/kg oil, a concentration of polychlorinated furans of 0.01–0.1 ng TEQ/kg oil, a concentration of polychlorinated biphenyls of 0.01–0.5 ng TEQ/kg oil, and a concentration of polycyclic aromatic hydrocarbons of 0.005–0.4 µg/kg in terms of BAP-equivalents.

24. A oil of marine origin according to claim 7, wherein said marine oil exhibits a concentration of polychlorinated dioxins of 0.03–0.22 ng TEQ/kg oil, a concentration of polychlorinated furans of 0.03–0.08 ng TEQ/kg oil, a concentration of polychlorinated biphenyls of 0.1–4 ng TEQ/kg oil, and a concentration of polycyclic aromatic hydrocarbons of 0.01–0.35 µg/kg in terms of BAP-equivalents.

25. A process according to claim 1, wherein c) is carried out a pressure of 2–30 mbar, and a temperature of 50–80° C. for a time period 10–100 minutes, and the amount of activated carbon added to the marine oil is 0.2–4.0% (w/w).

26. A process according to claim 1, wherein in e) 0.5–2.5% (w/w) of a filter aid is added to the marine oil and the activated carbon is separated from the marine oil by filtering.

27. A process according to claim 1, wherein the oil is deodorized at a temperature of 140 to 230° C. and under a pressure of 1–20 mbar.

* * * * *

UNITED STATES PATENT AND TRADEMARK OFFICE
CERTIFICATE OF CORRECTION

PATENT NO. : 6,469,187 B1 Page 1 of 1
APPLICATION NO. : 09/701841
DATED : October 22, 2002
INVENTOR(S) : Charles W. Craven It is certified that error appears in the above-identified patent and that said Letters Patent is hereby corrected as shown below:

Column 6, line 37, reads "(0.05" should read -- 0.05 --
Column 6, line 42, reads "wherein said is" should read -- wherein said oil is --

Signed and Sealed this

Nineteenth Day of August, 2008

JON W. DUDAS
*Director of the United States Patent and Trademark Office*